(12) United States Patent
Tetsuka

(10) Patent No.: US 7,300,341 B2
(45) Date of Patent: Nov. 27, 2007

(54) DENTAL GRINDING TOOL AND METHOD FOR MAKING THE SAME

(75) Inventor: Satoshi Tetsuka, Tochigi (JP)

(73) Assignee: Mani, Inc., Utsunomiya (JP)

( * ) Notice: Subject to any disclaimer, the term of this patent is extended or adjusted under 35 U.S.C. 154(b) by 0 days.

(21) Appl. No.: 11/511,448

(22) Filed: Aug. 29, 2006

(65) Prior Publication Data

US 2007/0049186 A1    Mar. 1, 2007

(30) Foreign Application Priority Data

Aug. 30, 2005    (JP) .............................. 2005-249614

(51) Int. Cl.
*B23F 21/03* (2006.01)
(52) U.S. Cl. ........................................ 451/548; 451/28
(58) Field of Classification Search .................. 451/28, 451/158–161, 353, 359, 548; 433/125
See application file for complete search history.

(56) References Cited

U.S. PATENT DOCUMENTS 4,834,655 A * 5/1989 Kyotani ..................... 433/166

6,186,789 B1 * 2/2001 Hugo et al. .................. 433/166
6,511,322 B1 * 1/2003 Kometas ...................... 433/166
7,021,933 B2 * 4/2006 Caldwell ...................... 433/165
7,144,253 B2 * 12/2006 Ikushima et al. ........... 433/166

FOREIGN PATENT DOCUMENTS

DE       296 08 197 U    8/1996
EP       0 284 173 A     9/1988
EP       0 528 592 A     2/1993

* cited by examiner

*Primary Examiner*—Dung VanNguyen
(74) *Attorney, Agent, or Firm*—Smith Patent Office

(57) ABSTRACT

The present invention provides a dental grinding tool which is unlikely to damage gums and capable of finely shaping a formation part on which a crown is placed, and further provides a method for making the same. The dental grinding tool is made by forming a chamferred part on the end portion of a columnar metal base 10, and fixing abrasive grains 2 onto the end face 10*a* of the metal base 10, wherein all of the abrasive grains 2 exist inside the outer circumferential line 10*d* of the end face 10*a* of the metal base 10. Grinding is performed only by the end face 10*a*. When a boundary part between teeth and gums is ground, only a chamferred part 10*c* which have no abrasive grains comes in contact with the gums. Therefore, the damage to the gums is prevented.

6 Claims, 4 Drawing Sheets

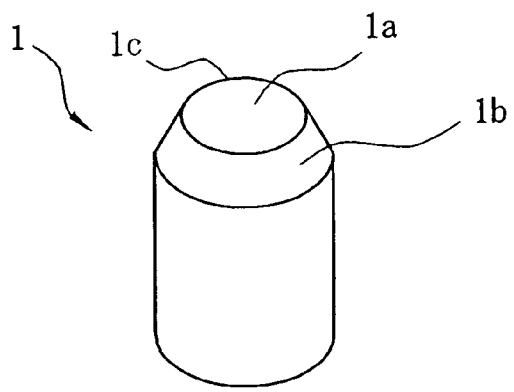
Fig. 4A
PRIOR ART
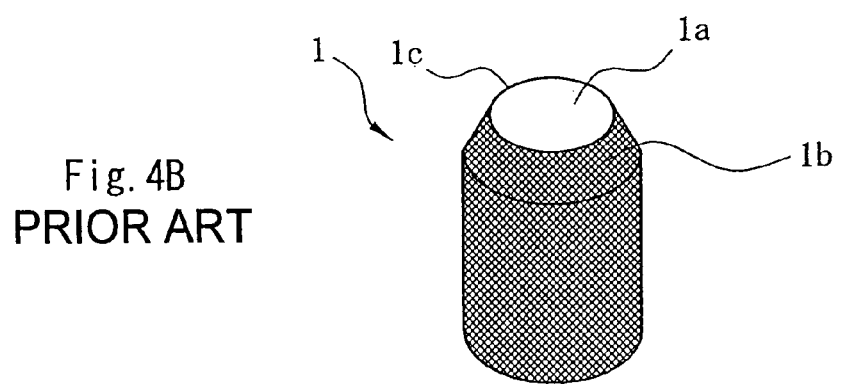
Fig. 4B
PRIOR ART
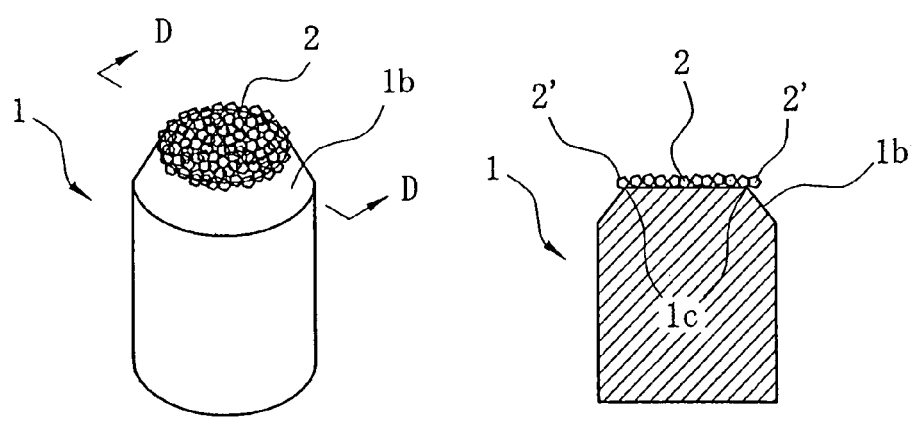
Fig. 4C
PRIOR ART
Fig. 4D
PRIOR ART

DENTAL GRINDING TOOL AND METHOD FOR MAKING THE SAME

BACKGROUND OF THE INVENTION

1. Field of the Invention

The present invention relates to a dental grinding tool, in particular a dental grinding tool which has a grinding part at the end face, and a method for making the same.

2. Description of the Related Art

In dental care or dental technique, a grinding tool which rotates at high speed by means of an air turbine is used. For this purpose, there is used a grinding tool which is made of steel or stainless steel and has a grinding part formed at the tip part of a cylindrical metal base. Diamond abrasive grains are usually fixed on the grinding part, and have most excellent abrasiveness in the field of grindstones. By driving the diamond grain-equipped grinding part by the air turbine, teeth and dental prostheses, such as crowns consisting of nickel-chromium castings, or the like, can be efficiently ground and processed.

Although the metal base of the grinding tool has usually a common cylindrical shape, the shape of the grinding part is diversified. For example, the grinding part may be cylindrical having the same diameter as that of the metal base, tapered becoming gradually thinner toward a tip part, spherical, etc. Further, the grinding part is classified into some classes by the size of the abrasive grains, such as coarse, intermediate and fine grains.

When a crown is placed on a tooth, a cross-hatched part "d" of the tooth "a" is removed with a grinding tool as shown in FIG. 3. Then, a formation part "c" which serves as a bonded surface with the crown is formed at a boundary part between the tooth "a" and the gum "b", an impression is taken to form the crown, and cement or the like, is filled between the crown and the tooth "a" for joining. In this joining, no gap is allowed between the formation part "c" and the bonded surface of the crown (not shown). When a gap is left, a larger amount of cement has to be used. This causes a problem that the cement dissolves after joining and the crown may be easily taken off. Therefore, if the formation part "c" is precisely and finely formed and an accurate impression is taken, no gap may be left between the crown and the joining surface, and the crown can be firmly fixed with a small amount of cement. For shaping this formation part "c", a grinding tool is used in which the end portion of a cylindrical metal base is chamferred into a truncated cone shape and a grinding part is formed by fixing abrasive grains only onto the end face of the metal base.

FIGS. 4A to 4D are diagrams for illustrating a conventional method for making such a grinding tool. First, as shown in FIG. 4A, a tapered chamferred part 1b is formed at the end portion of a cylindrical metal base 1 made of steel or stainless steel. Then, as shown in FIG. 4B, masking is applied on the outer surface other than the end face 1a of the metal base 1. This masking prevents abrasive grains 2 from adhering when the grains 2 are subsequently electrodeposited. The metal base 1 with the thus-applied masking is loaded into an electrodeposition apparatus, and diamond abrasive grains are electrodeposited only on the unmasked end face 1a by the composite plating method. The masking is subsequently removed to obtain a grinding tool in which the abrasive grains 2 are firmly fixed to the end face 1a, as shown in FIG. 4C.

However, it is difficult to apply masking by leaving only the end face unmasked. The masking is sometimes applied erroneously on the end face or unmasked parts (blanks) are left on the chamferred part. Therefore, by the conventional method, the end face is partly electrodeposited with the abrasive grains or the abrasive grains are electrodeposited on the chamferred part. When such a grinding tool is used, the boundary part between the tooth and the gums can not have a smooth and flat surface because the end face has an area where no abrasive grains are fixed or the abrasive grains fixed to the chamferred part may damage the gums when grinding the boundary part mentioned above. Thus such a grinding tool could not be used and was regarded as a defective product. For such a reason, rejection rate of the grinding tool has reached about 30% in the conventional manufacturing method.

If the abrasive grains were fixed to the end face and the grains were absent on the chamferred part 1b, the product was regarded at least as nondefective. Even in this nondefective product, however, some of the abrasive grains, grains 2', were protruding over an outer circumferential line 1c demarcating the end face 1a, as shown in FIG. 4C and FIG. 4D. These protruding grains 2' might often come in contact with the gums and damage the gums. Moreover, the formation part "c" to be created on the tooth by grinding could not be shaped finely. Consequently, it became impossible to obtain an accurate impression. This caused a problem that a gap was formed between the crown and the formation part "c".

Recently, stereomicroscopes are becoming increasingly popular, and dentists are now capable of confirming the formation part in more detail. Thus such a problem is growing more conspicuous and the solution of the problem is required.

SUMMARY OF THE INVENTION

The present invention has a configuration to achieve the above objectives and solve the above-described problems. In accordance with the objective, the present invention intends to provide a dental grinding tool which is unlikely to damage gums and capable of shaping a formation part finely, and to provide a method for making the same.

In order to attain the aforementioned objective, the dental grinding tool of the present invention is made by forming a chamferred part having a predetermined angle on the outer circumferential part of the end portion of a columnar metal base, and by fixing abrasive grains onto the end face of the metal base, wherein all of these abrasive grains exist inside the outer circumferential line of the end face of the metal base. The abrasive grains are diamond grains.

Furthermore, the present invention has another configuration to solve the above-described problems. In other words, the present invention provides a method for making a dental grinding tool having a chamferred part with a predetermined angle on the outer circumferential part of the end portion of a columnar metal base, and having abrasive grains on the end face of the metal base, comprising a step of forming the columnar metal base to have a predetermined length, a step of fixing the abrasive grains to the end face of the metal base and a step of grinding, to a tapered shape, the end portion of the metal base including the end face to which the abrasive grains are fixed.

The fixing step is performed by an electrodeposition method, and further including a step of masking the surface of the metal base other than the end face prior to the electrodeposition.

The present invention has still another configuration to solve the above-described problems. In other words, the present invention provides a method for making a dental grinding tool having a chamferred part with a predetermined angle on the outer circumferential part of the end portion of a columnar metal base, and having abrasive grains on the end face of the metal base, comprising a step of forming the columnar metal base to have a predetermined length, a step of grinding the end portion of the metal base to have a tapered shape, a step of placing on the metal base a masking cap which is elastic to cover the surface of the metal base other than the end face so that the end face of the metal base is exposed, and a step of fixing the abrasive grains only to the exposed end face.

In the present invention, the masking cap is hollow inside to come in press-contact with the surface of the metal base including the tapered-shaped end portion.

The present invention allows an accurate demarcation of a region which is capable of being ground, by preventing the grains from protruding from the outer circumferential line of the end face toward the outside. Consequently, the formation part can be shaped accurately and finely. Moreover, since the abrasive grains are completely absent on the side face of the grinding tool, the gums will not be damaged by these grains on the side face of the grinding tool.

BRIEF DESCRIPTION OF THE DRAWINGS

FIGS. 4A to 4C are diagrams illustrating how a conventional grinding tool is made, and FIG. 4D is a cross-sectional diagram of a conventional grinding tool shown in FIG. 4C along a line D-D.

DETAILED DESCRIPTION OF THE PREFERRED EMBODIMENTS

In the following, the embodiments of the present invention are described with reference to the accompanying drawings. FIGS. 1A to 1E are diagrams illustrating the dental grinding tool of the present invention, and a method for manufacturing the same.

Figure 1A:
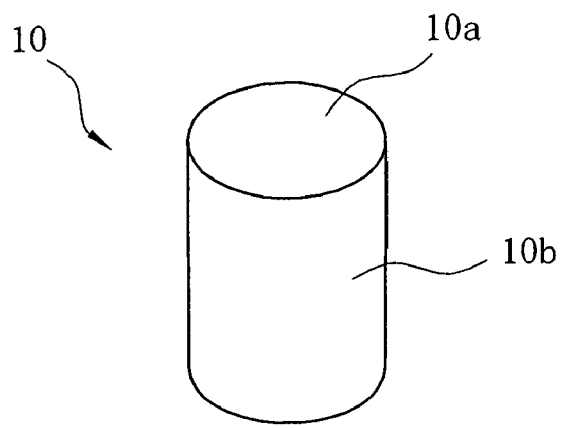
FIGS. 1A to 1D are diagrams illustrating a method for making the grinding tool of the present invention.

FIG. 1A is a perspective diagram of a metal base 10. In this example, the metal base 10 is obtained by cutting a cylindrical material made of stainless steel to a predetermined length. Besides stainless steel, various kinds of metallic materials and sintered compacts of tungsten carbide, silicon nitride, silicon carbide and the like can be used as a material. However, stainless steel yields an inexpensive and corrosion-resistant metal base. Moreover, when the metal base 10 is made of an electrically conductive material, the metal base 10 can be used as an electrode for electrodepositing abrasive grains, which will be described later.

In this example, the metal base 10 has a cylindrical shape. However, it may be used an elliptically columned or a polygonally columned one. However, it is preferable to use a cylindrical-shaped one because the grinding tool is used under rotation.

Figure 1B:
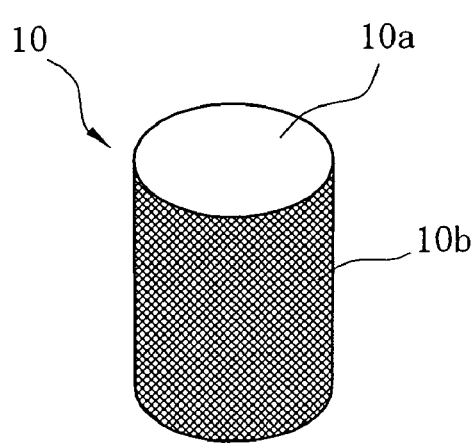

The metal base 10 is masked excluding a circular end face 10a, as shown in FIG. 1B. This masking is intended to prevent the abrasive grains 2 from adhering to a part except for the end face 10a when the grains 2 are fixed by subsequent electrodeposition.

Figure 1C:
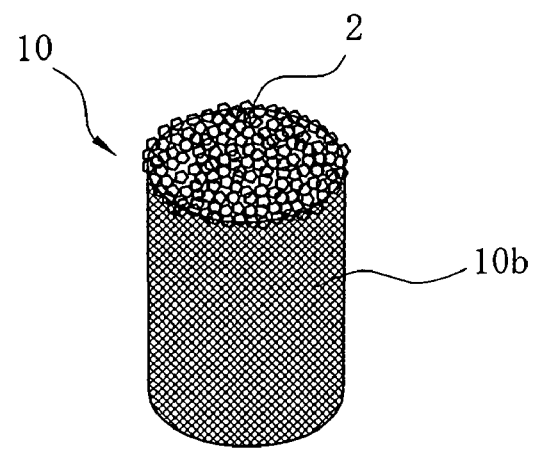

As shown in FIG. 1C, the abrasive grains 2 are fixed by electrodeposition to the end face 10a of the masked metal base 10. As the abrasive grains 2, it is desirable to use diamond grains so that teeth and nickel-chromium castings serving as dental prostheses can be efficiently ground.

The diamond abrasive grains are electrodeposited on the end face 10a by the composite plating method as will be described below. A usual composite plating method employs a plating bath consisting primarily of nickel sulfate. A mesh tub which contains grains having a particle diameter of 20 to 150 μm obtained by grinding natural diamond ore and classifying the resultant product according to its roughness, is immersed into the plating bath to obtain a plating liquid in which the diamond grains are dispersed uniformly by applying agitation or vibration. The metal base 10 is immersed in this plating liquid, and the diamond grains 2 are electrodeposited onto the end face 10a of the metal base 10 with constant distribution density by utilizing nickel as a binding phase which deposits by electrolytic plating.

As shown in FIG. 1C, the abrasive grains 2 are fixed in a state where some of the grains are protruding toward the outside of the end face 10a of the metal base 10. Moreover, although not illustrated, the side face 10b of the metal base 10 in the vicinity of the end face 10a is sometimes not masked or the masking occasionally peels off. The abrasive grains 2 may adhere also to these parts.

Figure 1D:
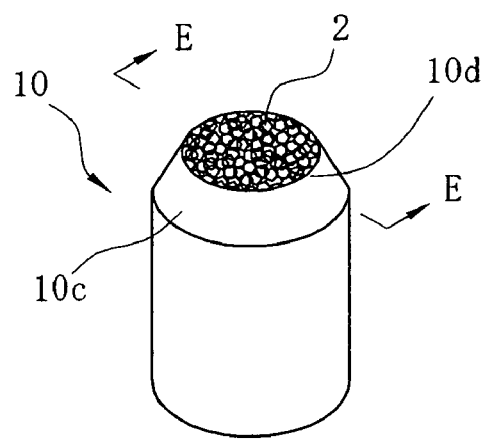
Figure 1E:
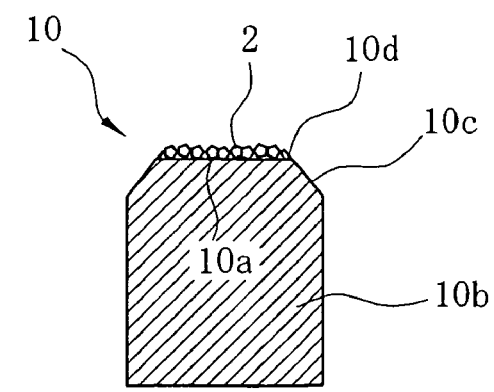
FIG. 1E is a cross-sectional view of the grinding tool shown in FIG. 1D along a line E-E.

As shown in FIG. 1D and FIG. 1E which is a sectional view taken in direction of the arrows E-E in FIG. 1D, a tapered chamferred part 10c is formed at the end portion of the metal base 10 by grinding the base 10 of FIG. 1C with a diamond grindstone which is not shown. The abrasive grains 2 which are fixed to the part of the side face 10b where no masking was applied are removed when the end portion is ground to form the chamferred part 10c. Moreover, with this grinding, an outer circumferential line 10d which demarcates the end face 10a is newly formed. As a result, the grains 2 which were located outside the outer circumferential line 10d are also removed altogether, and the protruding abrasive grains 2' once existed in the conventional grinding tool become nonexistent. Thereafter, the masking is removed to bring the grinding tool to completion.

In the above-described example, the chamferred part 10c is a tapered surface and change of the radius in the axial direction is linear. In place of the tapered surface it may be used a curved surface, such as a spherical surface, in which the radius varies non-linearly in the axial direction. Moreover, if the taper angle is made smaller and the diameter of the end face 10a is close to that of the metal base 10, a formation part "c" may be formed by grinding a tooth to a part very close to the boundary with gums.

The grinding tool of the present invention has a grinding part in which the abrasive grains 2 are fixed to the end face 10a. No abrasive grains are protruding from the outer circumferential line 10d of the end face 10a at all. Therefore, when the boundary part between the tooth and gums is ground with the grinding part of the grinding tool, only the chamferred part 10c having no abrasive grains comes in contact with the gums. Consequently, it becomes possible to shape the formation part without damaging the gums.

Figure 2A:
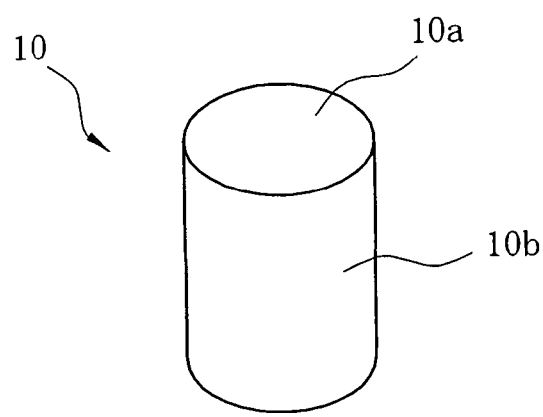
FIGS. 2A to 2D are diagrams illustrating another method for making the grinding tool of the present invention.
Figure 2B:
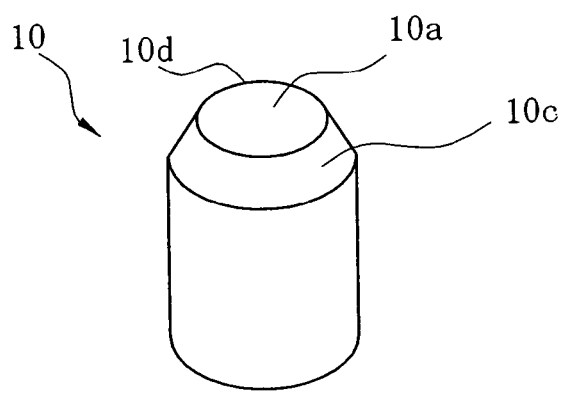
Figure 2C:
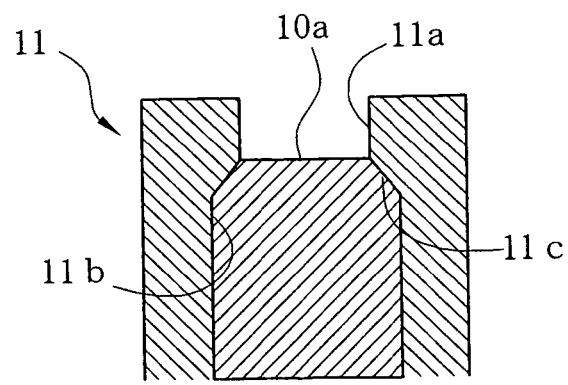
Figure 2D:
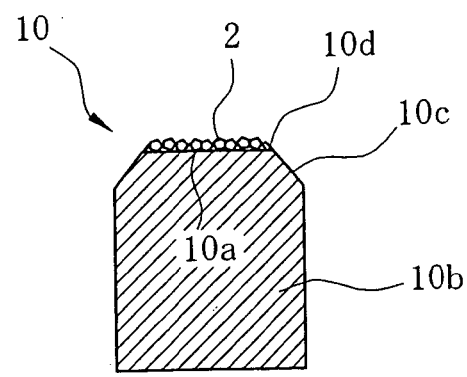
Figure 3:
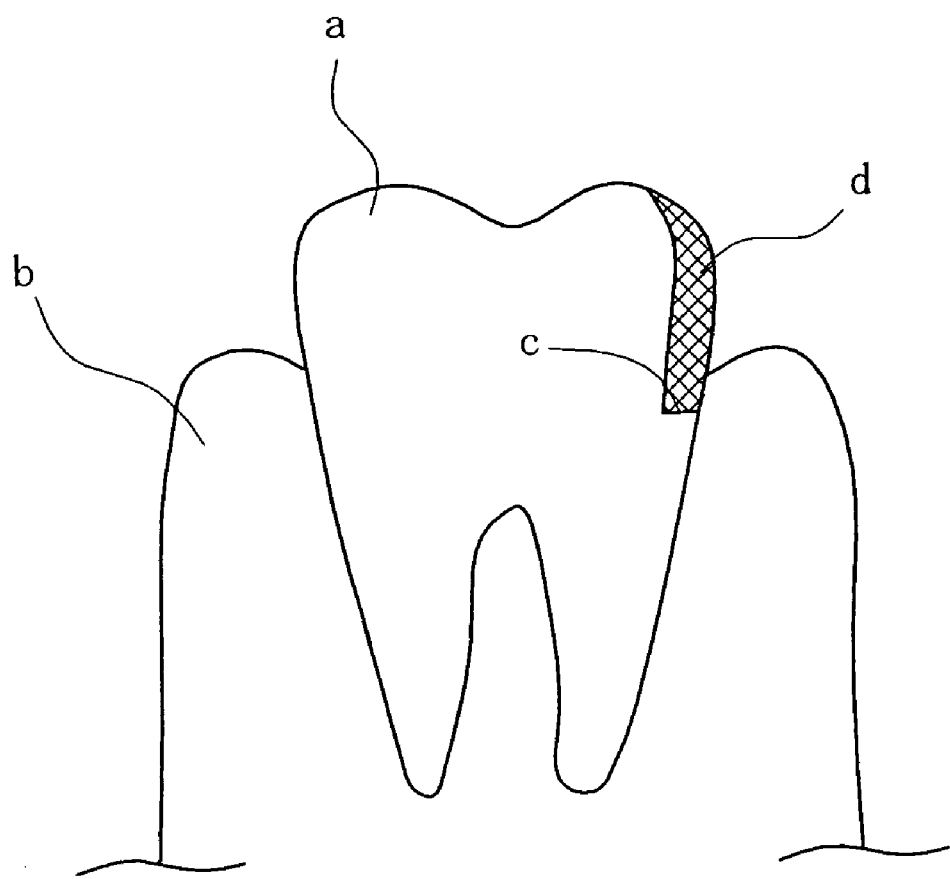
FIG. 3 is a diagram showing parts of a tooth to be ground with the grinding tool of the present invention.

FIGS. 2A to 2D show another method for manufacturing the grinding tool of the present invention. FIG. 2A is a perspective illustration of a metal base 10, which is identical with the metal base of FIG. 1A. As shown in FIG. 2B, a chamferred part 10c having a predetermined angle is formed on the circumferential part of the end portion of this metal base 10. As shown in FIG. 2C, a longitudinal sectional view, a hollow masking cap 11 consisting of a non-conductive material, such as plastic, is placed on the resultant metal base 10. The masking cap 11 is provided with a small-diameter part 11a through which the end face 10a of the metal base 10 is exposed neither more nor less than needed, a large-diameter hollow part 11b having practically the same diameter as the external diameter of the metal base 10, and a tapered part 11c formed between the parts 11a and 11b. The tapered part 11c matches the chamferred part 10c. When the masking cap 11 is placed as shown in FIG. 2C, the masking cap 11 comes in press-contact with the metal base 10 and the chamferred part 10c due to elasticity of the masking cap itself, and can cover these parts without leaving any space between them. Therefore, only the end face 10a of the metal base 10 is exposed. When the assembly of the metal base 10 and the masking cap 11 in this state is immersed in the plating liquid in which the diamond grains are dispersed uniformly, the grinding tool is formed, as shown in FIG. 2D, which has no protruding grains from the outer circumferential line 10d of the end face 10a.

In this manufacturing process it is sufficient to immerse only the end face 10a in the plating liquid, therefore the masking cap 11 should cover only the chamferred part 10c without necessarily covering the side face 10b of the metal base 10.

While the invention has been described with reference to particular example embodiments, further modifications and improvements which will occur to those skilled in the art, may be made within the purview of the appended claims, without departing from the scope of the invention in its broader aspect.

What is claimed is:

1. A dental grinding tool comprising:
    a columnar metal base having a predetermined length, a first end portion and a second end portion, the first end portion of said columnar metal base including an end face and a chamfered part having a predetermined angle on the first end portion of said columnar metal base,
    abrasive grains disposed on the end face of the first end portion of said columnar metal base,
    wherein the chamfered part defines a surface plane extending beyond the end face and all of said abrasive grains are disposed inside the surface plane of the chamfered part.

2. The dental grinding tool as described in claim 1, wherein said abrasive grains are diamond grains.

3. A method for making a dental grinding tool comprising the steps of:
    forming a columnar metal base having a predetermined length, a first end portion and a second end portion,
    fixing abrasive grains to an end face of the first end portion of the columnar metal base,
    grinding the first end portion of the columnar metal base after said step of fixing to have an end face and a chamfered part having a predetermined angle on the first end portion of the columnar metal base; and
    wherein the chamfered part defines a surface plane extending beyond the end face so that all of the abrasive grains are disposed inside the surface plane of the chamfered part.

4. The method for making a dental grinding tool as described in claim 3,
    wherein said fixing step is performed by an electrodeposition method, and further including a step of masking the surface of the metal base other than the end face prior to the electrodeposition.

5. A method for making a dental grinding tool comprising the steps of:
    forming a columnar metal base having a predetermined length, a first end portion and a second end portion,
    grinding the first end portion of the columnar metal base to have an end face and a chamfered part having a predetermined angle on the first end portion of the columnar metal base, the chamfered part defining a surface plane extending beyond the end face,
    disposing a masking cap over the columnar metal base so that the masking cap covers the surface of the columnar metal base including the chamfered part other than the end face so that the end face of the columnar metal base is exposed, and
    fixing the abrasive grains only to the end face exposed in the columnar metal base so that all of the abrasive grains are disposed inside the surface plane of the chamfered part.

6. The method for making a dental grinding tool as described in claim 5, wherein said step of disposing the masking cap includes press-contacting an inside surface of the masking cap to the surface of the metal base.

* * * * *